US012551638B2

(12) United States Patent
Li et al.

(10) Patent No.: US 12,551,638 B2
(45) Date of Patent: Feb. 17, 2026

(54) HEATING ASSEMBLY AND ELECTRONIC VAPORIZER

(71) Applicant: SHENZHEN SMOORE TECHNOLOGY LIMITED, Guangdong (CN)

(72) Inventors: Jun Li, Shenzhen (CN); Zhaohuan Zeng, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 619 days.

(21) Appl. No.: 18/081,241

(22) Filed: Dec. 14, 2022

(65) Prior Publication Data

US 2023/0201491 A1 Jun. 29, 2023

(30) Foreign Application Priority Data

Dec. 27, 2021 (CN) ......................... 202123320550.6

(51) Int. Cl.
*A61M 15/06* (2006.01)
*A24F 40/20* (2020.01)
(Continued)

(52) U.S. Cl.
CPC ............. *A61M 15/06* (2013.01); *A24F 40/20* (2020.01); *A24F 40/46* (2020.01); *A24F 40/53* (2020.01);
(Continued)

(58) Field of Classification Search
CPC ..... A61M 15/06; A41M 11/042; A24F 40/53; A24F 40/20; A24F 40/60; A42F 40/46; H05B 3/06
See application file for complete search history.

(56) References Cited

U.S. PATENT DOCUMENTS

2011/0147486 A1* 6/2011 Greim ...................... H05B 3/18 29/611
2015/0257445 A1* 9/2015 Henry, Jr. ............... A24F 40/50 131/328
(Continued)

FOREIGN PATENT DOCUMENTS

CN 108378427 A 8/2018
CN 110708974 A 1/2020
(Continued)

OTHER PUBLICATIONS

European Patent Office, Search Report in European Patent Application No. 22213862.0 (May 22, 2023).
(Continued)

*Primary Examiner* — Clinton T Ostrup
(74) *Attorney, Agent, or Firm* — Leydig, Voit & Mayer, Ltd.

(57) ABSTRACT

A heating assembly for heat an aerosol-generation substrate, including: a heating cavity having: a first conductive region; a second conductive region provided on a side of the first conductive region; and an insulating region provided between the first conductive region and the second conductive region for electrically isolating the first conductive region from the second conductive region. In a state where the aerosol-generation substrate is accommodated in the heating cavity, an electrical connection is formed between the first conductive region and the second conductive region through the aerosol-generation substrate.

18 Claims, 4 Drawing Sheets

(51) Int. Cl.

| | |
|---|---|
| ***A24F 40/46*** | (2020.01) |
| ***A24F 40/53*** | (2020.01) |
| ***A24F 40/60*** | (2020.01) |
| ***A61M 11/04*** | (2006.01) |
| ***H05B 3/06*** | (2006.01) |

(52) U.S. Cl.

CPC ........... *A24F 40/60* (2020.01); *A61M 11/042* (2014.02); *H05B 3/06* (2013.01); *H05B 2203/016* (2013.01)

(56) References Cited

U.S. PATENT DOCUMENTS

| | | | | |
|---|---|---|---|---|
| 2015/0258289 | A1* | 9/2015 | Henry, Jr. | A61M 15/06 128/202.21 |
| 2017/0119052 | A1* | 5/2017 | Williams | H05B 3/44 |
| 2020/0315255 | A1 | 10/2020 | Zhou et al. | |
| 2021/0100289 | A1 | 4/2021 | Johaentges | |
| 2023/0201491 | A1* | 6/2023 | Li | H05B 3/42 128/202.21 |

FOREIGN PATENT DOCUMENTS

| | | | | | |
|---|---|---|---|---|---|
| CN | 111109684 | A | * | 5/2020 | A24D 1/20 |
| CN | 112315031 | A | | 2/2021 | |
| EP | 3280280 | | | 2/2018 | |
| EP | 4082363 | A1 | * | 11/2022 | A24D 1/20 |
| EP | 4218448 | A1 | * | 8/2023 | A24F 40/46 |
| EP | 4393331 | A1 | * | 7/2024 | A24F 40/40 |
| JP | 2021521834 | A | | 8/2021 | |
| JP | 2021535742 | A | * | 12/2021 | A24F 40/50 |
| JP | 7399890 | B2 | * | 12/2023 | A24F 40/465 |
| KR | 1020210006399 | A | | 1/2021 | |
| KR | 1020210143576 | A | | 11/2021 | |
| KR | 102509092 | B1 | * | 3/2023 | H05B 6/36 |
| WO | 2016162446 | A1 | | 10/2016 | |
| WO | WO-2019234143 | A1 | * | 12/2019 | A24F 40/20 |
| WO | 2020201295 | A1 | | 10/2020 | |
| WO | 2021069526 | A1 | | 4/2021 | |
| WO | 2021180815 | A1 | | 9/2021 | |
| WO | 2021186603 | A1 | | 9/2021 | |
| WO | WO-2021235711 | A1 | * | 11/2021 | H05B 6/36 |
| WO | WO-2024002967 | A1 | * | 1/2024 | A24F 40/20 |

OTHER PUBLICATIONS

Japanese Patent Office, Notice of Reasons for Refusal in Japanese Patent Application No. 2022-189978 (Nov. 21, 2023).

Korean Patent Office, Written Decision on Registration in Korean Patent Application No. 10-2022-0151627 (May 20, 2025).

* cited by examiner

HEATING ASSEMBLY AND ELECTRONIC VAPORIZER

CROSS-REFERENCE TO PRIOR APPLICATION

Priority is claimed to Chinese Patent Application No. 202123320550.6, filed on Dec. 27, 2021, the entire disclosure of which is hereby incorporated by reference herein.

FIELD

The present invention relates to the field of vaporization technologies, and in particular, to a heating assembly and an electronic vaporizer.

BACKGROUND

An aerosol is a colloidal dispersion system formed by solid or liquid small particles dispersed and suspended in an air medium. Since the aerosol can be absorbed by a human body through a respiratory system, a novel alternative absorption manner is provided for a user. For example, an electronic vaporization device that generates aerosols through an aerosol substrate can be used in different fields such as the medical field, to deliver inhalable aerosols to the user, thereby replacing a conventional product form and an absorption manner.

Currently, an electronic vaporizer configured to bake a solid aerosol-generation substrate is usually provided with a heating cavity configured to accommodate the aerosol-generation substrate. When using the electronic vaporizer, the user needs to insert the aerosol-generation substrate into the heating cavity, and then presses a start button to start the electronic vaporizer to bake the aerosol-generation substrate, resulting in relatively cumbersome operations.

SUMMARY

In an embodiment, the present invention provides a heating assembly configured to heat an aerosol-generation substrate, comprising: a heating cavity, comprising: a first conductive region; a second conductive region provided on a side of the first conductive region; and an insulating region provided between the first conductive region and the second conductive region and configured to electrically isolate the first conductive region from the second conductive region, wherein, in a state where the aerosol-generation substrate is accommodated in the heating cavity, an electrical connection is formed between the first conductive region and the second conductive region through the aerosol-generation substrate.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
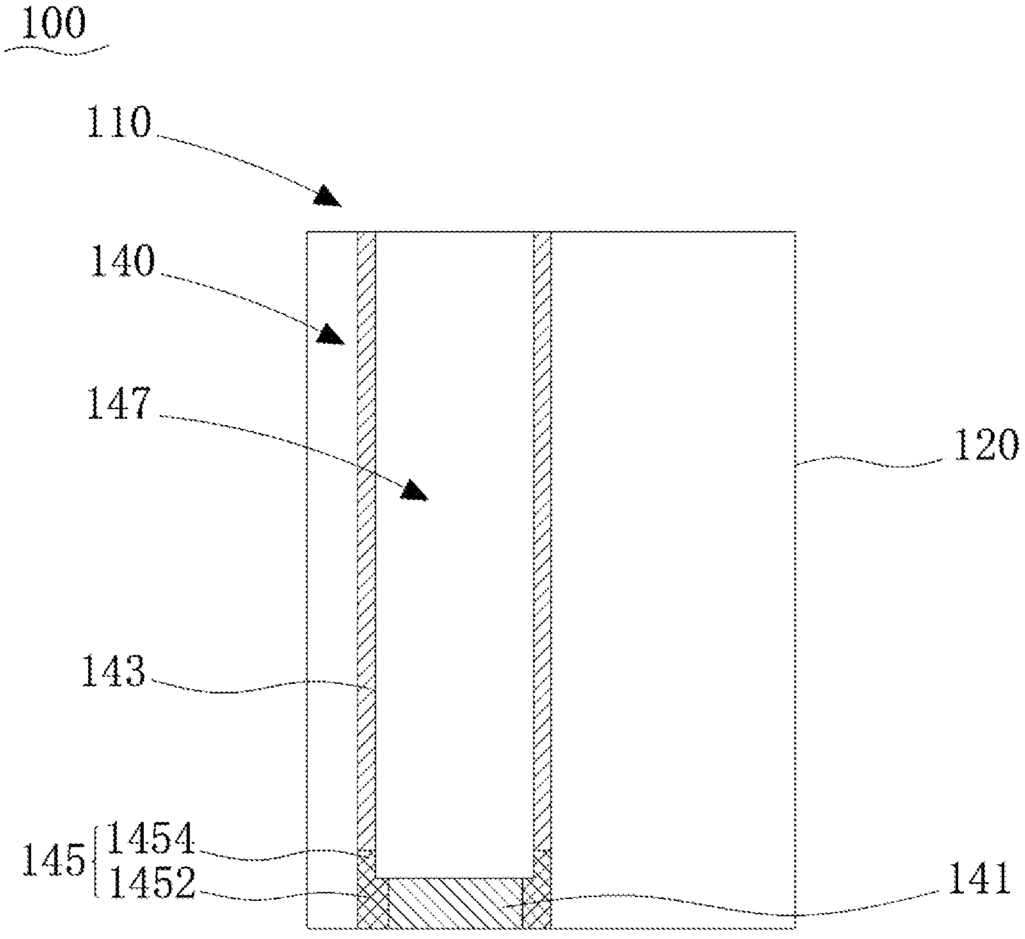
FIG. 1 is a schematic structural diagram of a heating assembly according to an embodiment of the present invention.

In an embodiment, to resolve the problems that a detection method for detecting insertion of an aerosol-generation substrate is relatively complex and reliability of a detection structure is relatively poor, the present invention provides a heating assembly and an electronic vaporizer. By using the heating assembly and the electronic vaporizer, technical effects of simplifying the detection method and improving the reliability of the detection structure can be achieved.

According to an aspect of this application, a heating assembly is provided, which is configured to heat the aerosol-generation substrate. The heating assembly includes a heating cavity and the heating cavity includes:

- a first conductive region;
- a second conductive region, provided on a side of the first conductive region; and
- an insulating region, provided between the first conductive region and the second conductive region and configured to electrically isolate the first conductive region from the second conductive region;
- where in a state where the aerosol-generation substrate is accommodated in the heating cavity, an electrical connection is formed between the first conductive region and the second conductive region through the aerosol-generation substrate.

In an embodiment, the heating cavity includes a first end and a second end that are arranged opposite to each other. The aerosol-generation substrate is inserted into the second end from the first end, and the first conductive region is provided on a side of the second conductive region facing the second end.

In an embodiment, the first conductive region is provided at the second end of the heating cavity, and the second conductive region is provided on a cavity side wall of the heating cavity.

In an embodiment, one end of the second conductive region is connected to the insulating region, and the other end of the second conductive region extends to the first end of the heating cavity in a direction away from the insulating region.

In an embodiment, the heating assembly includes a first structural member, a second structural member, and an insulating member, where the first structural member is constructed to form a part of a cavity bottom wall of the heating cavity, and at least a part of the first structural member forms the first conductive region;

- the second structural member is constructed to form a part of a cavity side wall of the heating cavity, and at least a part of the second structural member forms the second conductive region; and
- the insulating member is arranged between the first structural member and the second structural member, and the insulating member forms the insulating region.

In an embodiment, the first structural member is entirely made of a conductive material, and/or the second structural member is entirely made of a conductive material.

In an embodiment, the insulating member includes an insulating bottom wall and an insulating side wall formed by extending from the insulating bottom wall in the same direction. The insulating side wall surrounds the insulating bottom wall in a circumferential direction to form an insulating accommodating cavity. The insulating bottom wall is provided with a run-through mounting hole in communication with the insulating accommodating cavity. The first structural member is accommodated in the mounting hole.

In an embodiment, an inner diameter of the mounting hole is less than an inner diameter of the insulating accommodating cavity.

According to an aspect of this application, an electronic vaporizer is provided, including a battery assembly and the foregoing heating assembly. The heating assembly is electrically connected to the battery assembly.

In an embodiment, the electronic vaporizer further includes a vibration unit. When the first structural member and the second structural member transmit electrical signals through the aerosol-generation substrate, the vibration unit vibrates.

Through provision of the first conductive region, the second conductive region, and the insulating region in the heating cavity, the heating assembly can accurately detect whether there is an aerosol-generation substrate being accommodated in the heating cavity without a manual operation by a user, which is high in ease of use and reliability, and prevents the aerosol-generation substrate from being excessively squeezed, thereby eliminating the risk of damaging the aerosol-generation substrate. In addition, a structure of a heating cylinder is simple, and therefore there is no need to add too many components such as an electromagnetic induction coil, thereby enabling production cost to be lower and assembly efficiency to be higher.

100, Electronic vaporizer; 110, heating assembly; 120, main housing; 140, heating cylinder; 141, first structural member; 143, second structural member; 145, insulating member; 1452, insulating bottom wall; 1454, insulating side wall; and 147, heating cavity.

To make the foregoing objectives, features and advantages of the present invention more comprehensible, detailed description is made to specific implementations of the present invention below with reference to the accompanying drawings. In the following description, many specific details are described to give a full understanding of the present invention. However, the present invention may be implemented in many other manners different from those described herein. A person skilled in the art may make similar improvements without departing from the connotation of the present invention. Therefore, the present invention is not limited to the specific embodiments disclosed below.

In the description of the present invention, it should be understood that orientation or position relationships indicated by the terms such as "length", "above", "below", "vertical", "horizontal", "top", "bottom", "inner", "outer", "clockwise", "counterclockwise", "axial", "radial", and "circumferential" are based on orientation or position relationships shown in the accompanying drawings, and are merely used for describing the present invention and simplifying the description, rather than indicating or implying that the mentioned apparatus or element should have a particular orientation or be constructed and operated in a particular orientation. Therefore, such terms should not be construed as limiting of the present invention.

In addition, the terms "first" and "second" are used for descriptive purposes only and are not to be construed as indicating or implying relative importance or implicitly indicating the number of technical features indicated. Therefore, features defining "first" and "second" can explicitly or implicitly include at least one of the features. In the description of the present invention, unless otherwise explicitly defined, "a plurality of" means at least two, for example, two, three, and the like.

In the present invention, unless otherwise explicitly specified and defined, terms such as "mounted", "connected", "connection", and "fixed" should be understood in broad sense, for example, the connection may be a fixed connection, a detachable connection, or an integral connection; or the connection may be a mechanical connection or an electrical connection; or the connection may be a direct connection, an indirect connection through an intermediary, or internal communication between two elements or a mutual action relationship between two elements, unless otherwise specified explicitly. A person of ordinary skill in the art can understand specific meanings of the terms in the present invention according to specific situations.

In the present invention, unless explicitly specified or limited otherwise, a first feature being located "above" or "below" a second feature may be the first feature being in a direct contact with the second feature, or the first feature being in an indirect contact with the second feature through an intermediate medium. Moreover, the first feature "over", "above" and "up" the second feature may be that the first feature is directly above or obliquely above the second feature, or simply indicates that a horizontal height of the first feature is higher than that of the second feature. The first feature "under", "below" and "down" the second feature may be that the first feature is directly below or obliquely below the second feature, or simply indicates that a horizontal height of the first feature is less than that of the second feature.

It should be noted that, when an element is referred to as "being fixed to" or "being arranged on" another element, the element may be directly on the another element, or an intermediate element may be present. When an element is considered to be "connected to" another element, the element may be directly connected to the another element, or an intermediate element may also be present. The terms "vertical", "horizontal", "above", "below", "left", "right" and similar expressions used in this specification are only for purposes of illustration but not indicate a unique implementation.

Figure 2:
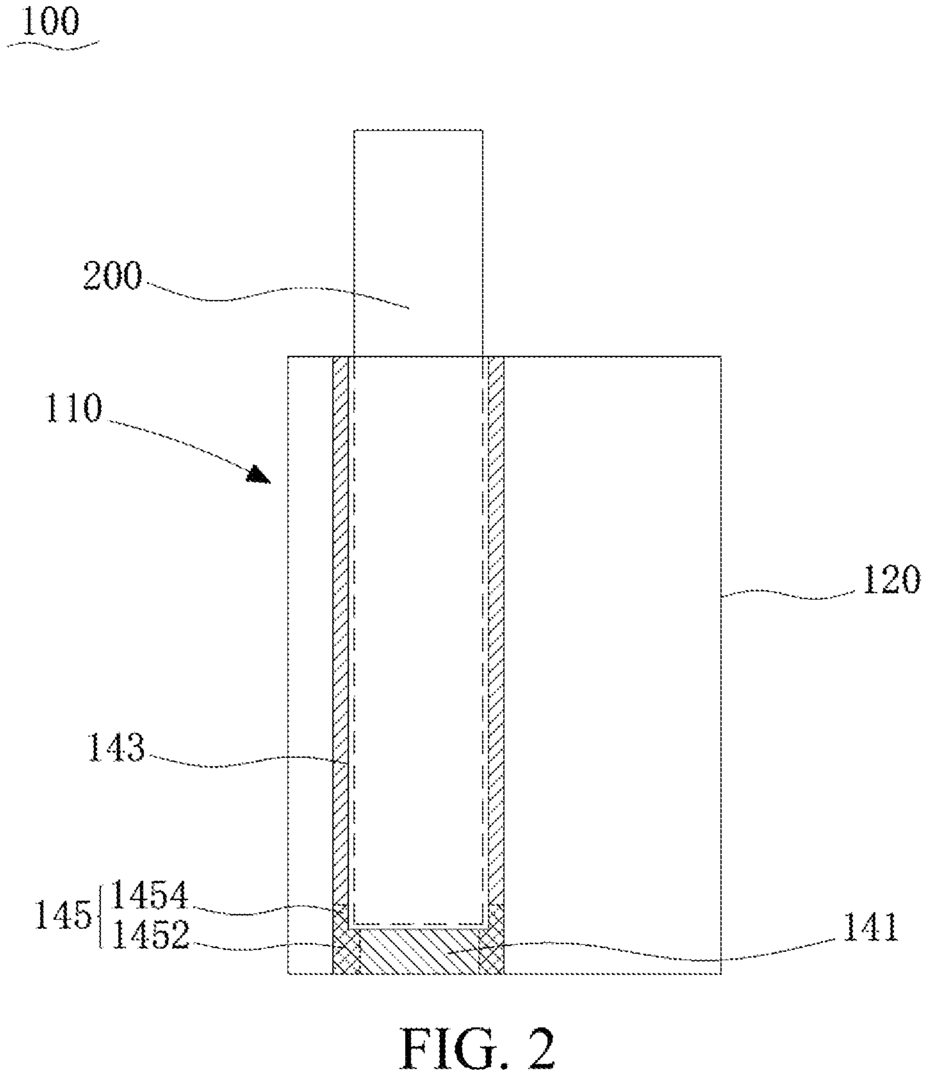
FIG. 2 is a schematic structural diagram in which the heating assembly shown in FIG. 1 is inserted with an aerosol-generation substrate.

Referring to FIG. 1 and FIG. 2, an embodiment of the present invention provides an electronic vaporizer 100, including a battery assembly and a heating assembly 110. An aerosol-generation substrate 200 may be inserted into the heating assembly 110, and the heating assembly 110 heats the solid aerosol-generation substrate 200 under an action of electrical energy of a battery, to generate aerosols for a user to inhale. Specifically, in the following embodiments, the aerosol-generation substrate 200 is in a cylindrical solid structure.

As described in the background, the method used by the current electronic vaporizer for detecting whether there is an aerosol-generation substrate being inserted is relatively complex and low in reliability, which hinders the promotion and application of the electronic vaporizer to some extent.

For example, some electronic vaporizers include a control button for outputting insertion signals. After the aerosol-generation substrate is inserted into the electronic vaporizer, the control button need to be manually pressed to output the insertion signals. In this manner, the electronic vaporizer is inconvenient to use. Moreover, the control button is prone to malfunction after being pressed for a long time, and consequently the electronic vaporizer fails to be used normally.

Some electronic vaporizers are mounted with winding coils and electromagnetic detection circuits, and have a layer of metal foil arranged inside the aerosol-generation substrate. The winding coils generate the insertion signals after the aerosols generate substrate. In this manner, additional winding coils and electromagnetic detection circuits need to be added, which increases production costs and volumes of the electronic vaporizers.

Some electronic vaporizers are mounted with squeeze-type mechanical switches. The mechanical switches may be squeezed to generate the insertion signals when the aerosol-generation substrates are inserted into the electronic vaporizers. However, since the aerosol-generation substrates are squeezed, there is a risk of causing damage to the aerosol-generation substrates. In addition, an assembly manner of the mechanical switches is relatively complex, thereby reducing the assemble efficiency of the electronic vaporizers.

Some electronic vaporizers are further mounted with photoelectric switches. Light emitted by the photoelectric switches may be reflected to generate insertion signals after the aerosol-generation substrates are inserted into the electronic vaporizers. However, the photoelectric switches can only operate stably when being mounted close to the aerosol-generation substrates. Since temperatures around the aerosol-generation substrates are relatively high, stable operation of the photoelectric switches are easily affected. In addition, after using the aerosol-generation substrates, residual aerosol-generation substrates tend to interfere with normal operation of the photoelectric switches.

To resolve the above problems, still referring to FIG. 1 and FIG. 2, the heating assembly 110 includes a main housing 120, which includes a heating cavity 147 with an opening at one end. The heating cavity 147 is configured to accommodate the aerosol-generation substrate 200. The electronic vaporizer 100 further includes a detection unit. The detection unit is electrically connected to the heating assembly 110, and is configured to determine whether there is the aerosol-generation substrate 200 being accommodated in a heating cylinder 140, thereby controlling an operating state of the electronic vaporizer.

Specifically, the heating cavity 147 includes a first conductive region, a second conductive region, and an insulating region. The second conductive region is provided on a side of the first conductive region. The first conductive region and the second conductive region can respectively be used as a transceiver for performing capacitive sensing and a transceiver for performing resistance measurement, to receive and transmit a capacitive sensing signal and a resistance change signal. The insulating region is provided between the first conductive region and the second conductive region and is configured to electrically isolate the first conductive region from the second conductive region.

The detection unit is configured to detect a capacitive sensing signal and a resistance signal between the first conductive region and the second conductive region, and to output an insertion signal according to the capacitive sensing signal and the resistance signal.

In a state where there is no aerosol-generation substrate 200 in the heating cavity 147, the first conductive region is electrically isolated from the second conductive region by the insulating region. Therefore, the first conductive region and the second conductive region cannot form an electrical signal loop. In this case, the capacitive sensing signal and the resistance signal between the first conductive region and the second conductive region are obtained by the detection unit, and are respectively marked as C1 and R1. In a state where there is the aerosol-generation substrate 200 being accommodated in the heating cavity 147, the aerosol-generation substrate 200 improves electrical conductivity of the first conductive region and the second conductive region. An electrical connection is formed between the first conductive region and the second conductive region through the solid aerosol-generation substrate 200, thereby changing magnitude of the capacitive sensing signal and the resistance signal between the first conductive region and the second conductive region. In this case, the capacitive sensing signal and the resistance signal between the first conductive region and the second conductive region are obtained by the detection unit, and are respectively marked as C2 and R2. The detection unit obtains differences (that is, a difference between C1 and C2, and a difference between R1 and R2) between values measured before and after by filtering through an algorithm, then determines whether there is the aerosol-generation substrate 200 being accommodated in the heating cavity 147 by determining sizes of the measurement differences and a preset calibration difference.

In this way, through provision of the first conductive region, the second conductive region, and the insulating region in the heating cavity 147, the heating assembly 110 can accurately detect whether there is the aerosol-generation substrate 200 being accommodated in the heating cavity 147 without a manual operation by a user, which is high in ease of use and reliability, and prevents the aerosol-generation substrate 200 from being excessively squeezed, thereby eliminating the risk of damaging the aerosol-generation substrate 200. In addition, a structure of the heating assembly 110 is simple, and therefore there is no need to add too many components such as an electromagnetic induction coil, thereby enabling the production cost to be lower and the assembly efficiency to be higher.

In some embodiments, the detection unit is a capacitance detection chip or a resistance detection chip. The detection unit is usually in a standby state, and is woke up at regular intervals to perform detection. An interval time preferably ranges from 0.1 second to 1 second. In an optional embodiment, if the detection unit detects the existence of the aerosol-generation substrate 200, detection is performed repeatedly for many times. If the existence aerosol-generation substrate 200 is detected each time, it is determined that there is the aerosol-generation substrate 200 being accommodated in the heating cavity 147, thus outputting the insertion signal to cause the heating assembly 110 to generate heat to heat the aerosol-generation substrate 200.

In some embodiments, the heating cavity 147 includes a first end and a second end that are arranged opposite to each other. The first end is an end of the heating cavity at which an opening end is provided to be in communication with an external environment, and the second end is an end of the heating cavity 147 at which a cavity bottom wall is arranged. The aerosol-generation substrate is inserted into the second end from the first end of the heating cavity 147. The first conductive region is provided on a side of the second conductive region facing the second end. That is, during insertion of the aerosol-generation substrate 200, the aerosol-generation substrate 200 first comes into contact with the first conductive region, and then comes into contact with the second conductive region. Finally, a part of the aerosol-generation substrate 200 is in contact with the first conductive region, and an other part of the aerosol-generation substrate 200 is in contact with the second conductive region, to implement the electrical connection between the first conductive region and the second conductive region. Since the electrical connection between the first conductive region and the second conductive region can be implemented only when the aerosol-generation substrate 200 is simultaneously in contact with the first conductive region and the second conductive region, a range of a heating area of the aerosol-generation substrate 200 may be controlled by setting a position of the second conductive region, to implemented different heating requirements.

As a preferred implementation, the first conductive region is provided at the second end of the heating cavity 147, and the second conductive region is provided on a cavity side wall of the heating cavity 147. In addition, one end of the second conductive region is connected to the insulating region, and an other end of the second conductive region extends to the second end of the heating cavity 147 in a direction away from the insulating region. Since the first conductive region is provided at the second end of the heating cavity 147, when and only when the aerosol-generation substrate 200 is inserted into the bottom of the heating cavity 147 to be in contact with the first conductive region, the first conductive region can be electrically connected to the second conductive region through the solid aerosol-generation substrate 200. In this case, it is avoided that the aerosol-generation substrate 200 is heated when the aerosol-generation substrate 200 is not inserted in place, thereby preventing a position of a heating area from offsetting because the aerosol-generation substrate 200 is not completely inserted into the heating cavity 147. Therefore, the heating effect of the heating assembly 110 is ensured.

As shown in FIG. 1, specifically, in some embodiments, the heating assembly 110 includes the heating cylinder 140 arranged in the main housing 120. The heating cylinder 140 has a substantially cylindrical structure to form the heating cavity 147. Specifically, the heating cylinder 140 includes a first structural member 141, a second structural member 143, and an insulating member 145. The first structural member 141 is constructed to form a part of the cavity bottom wall of the heating cavity 147, and at least a part of the first structural member 141 forms the first conductive region. The second structural member 143 is constructed to form a part of the cavity side wall of the heating cavity 147, and at least a part of the second structural member 143 forms the second conductive region. The insulating member 145 is arranged between the first structural member 141 and the second structural member 143, and the insulating member 145 forms the insulating region.

Specifically, the first structural member 141 has a solid cylindrical structure and is entirely made of a conductive material. An upper surface of the first structural member 141 forms a part of the cavity bottom wall of the heating cavity 147, and the first structural member 141 forms the first conductive region.

The insulating member 145 has a hollow rotating body structure. The insulating member 145, which is entirely made of an insulating material, includes an insulating bottom wall 1452 and an insulating side wall 1454 formed by extending from the insulating bottom wall 1452 in the same direction. The insulating side wall 1454 surrounds the insulating bottom wall 1452 in a circumferential direction to form an insulating accommodating cavity. The insulating bottom wall 1452 is provided with a run-through mounting hole in communication with the insulating accommodating cavity. The mounting hole and the insulating accommodating cavity are coaxially arranged, and an inner diameter of the mounting hole is less than an inner diameter of the insulating accommodating cavity. The first structural member 141 is accommodated in the mounting hole. An upper surface of the insulating bottom wall 1452 surrounds the upper surface of the first structural member 141 to form an other part of the cavity bottom wall. An inner surface of the insulating side wall 1454 forms a part of the cavity side wall of the heating cavity 147. The insulating member 145 forms the insulating region.

The second structural member 143 has a hollow tubular structure and is entirely supported by a conductive material. One end of the second structural member 143 is connected to the insulating side wall 1454, and the other end of the second structural member 143 extends vertically in a direction away from the first structural member 141, to form a hollow cylindrical structure and be in communication with the insulating accommodating cavity. In addition, an inner diameter of the second structural member 143 is the same as an inner diameter of the insulating member 145. An inner surface of the second structural member 143 forms an other part of the cavity bottom wall of the heating cavity 147, and the second structural member 143 forms the second conductive region.

In this way, the insulating member 145, the first structural member 141, and the second structural member 143 jointly form the heating cavity 147 with an opening at one end. The insulating bottom wall 1452 and the first structural member 141 jointly form the cavity bottom wall of the heating cavity 147, and the insulating side wall 1454 and the second structural member 143 jointly from the cavity side wall of the heating cavity 147. One end of the aerosol-generation substrate 200 passes through the second structural member 143 to be abutted against the first structural member 141. The second structural member 143 is coated on an outer circular surface of the aerosol-generation substrate 200, so that the aerosol-generation substrate 200 may serve to increase a resistance value and a capacitance value between the first structural member 141 and the second structural member 143. A size of the first structural member 141 and a size of the mounting hole matching the first structural member may be adjusted as required, to further adjust a minimum gap between the first structural member 141 and the second structural member 143, thereby avoiding a case of mistaken triggering caused by an excessive short distance between the first structural member 141 and the second structural member 143.

Figure 3:
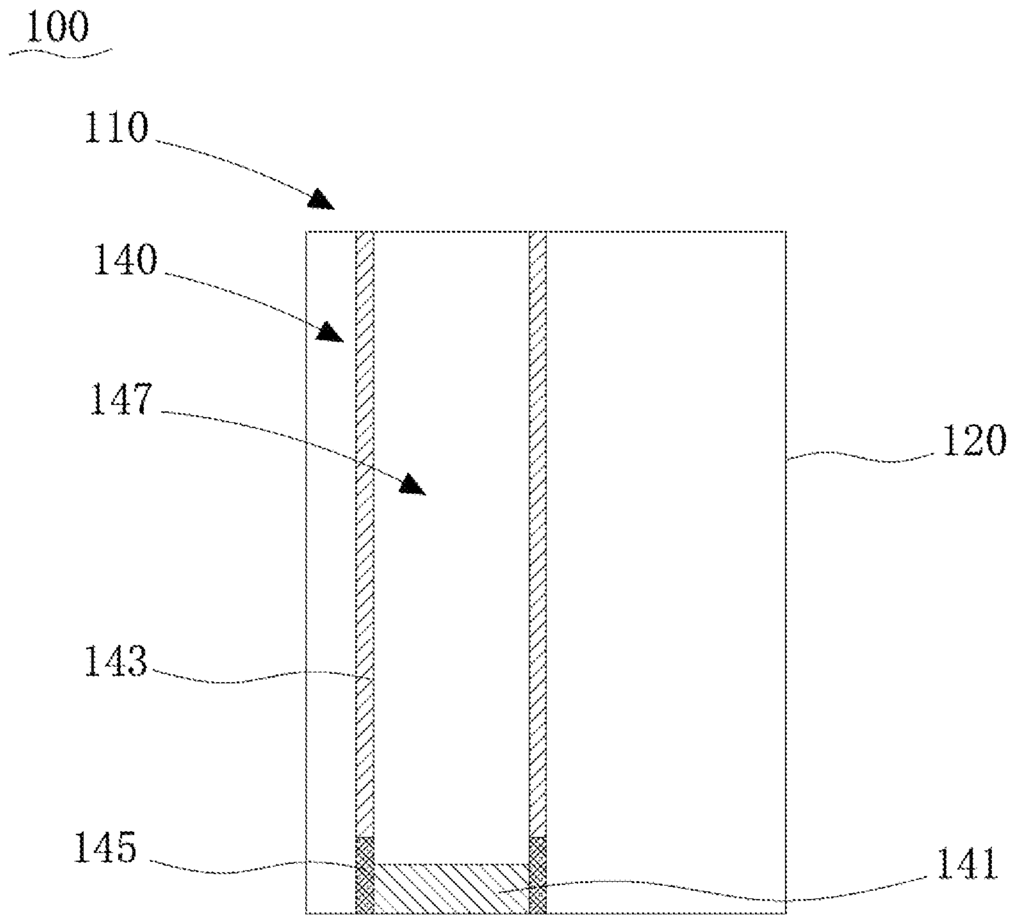
FIG. 3 is a schematic structural diagram of a heating assembly according to another embodiment of the present invention.

As shown in FIG. 3, in some other embodiments, the insulating member 145 has a tubular structure with openings at two ends, and inner diameters of the insulating member 145 are equal everywhere. The first structural member 141 is accommodated in the insulating member 145. In addition, the insulating member 145 whose axial length is greater than an axial length of the insulating member 145 extends out of the first structural member 141 and faces one end of the opening end of the heating cavity 147.

Figure 4:
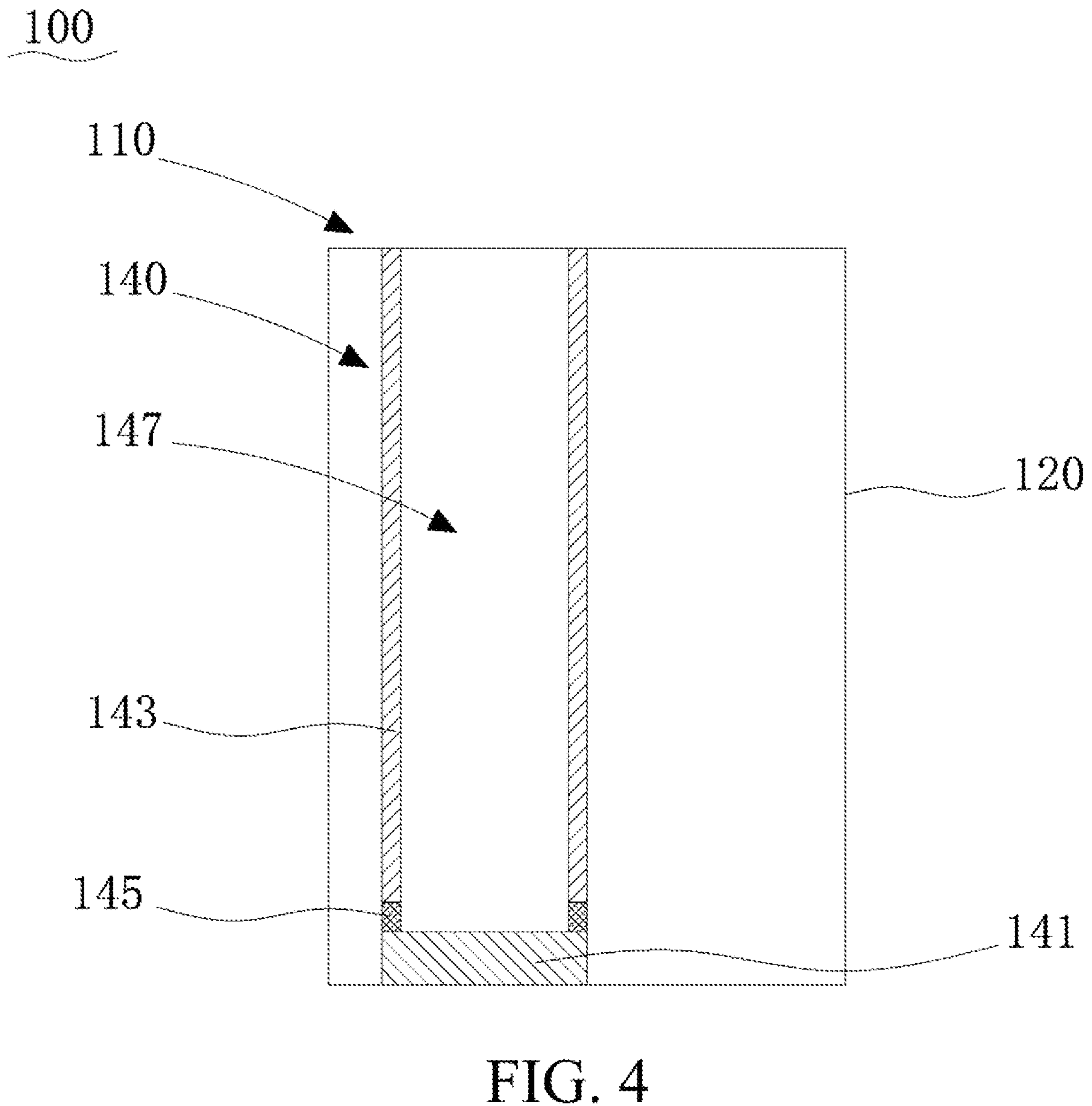
FIG. 4 is a schematic structural diagram of a heating assembly according to still another embodiment of the present invention. Description of reference numerals.

As shown in FIG. 4, in some other embodiments, the insulating member 145 is provided between the first structural member 141 and the second structural member 143. The insulating member 145 is in the tubular structure with the openings at two ends. The first structural member 141 and the second structural member 143 respectively abut against the two opposite ends of the insulating member 145.

In some embodiments, both the first conductive region and the second conductive region are formed by a conductive film layer formed in the main housing, to replace the first structural member 141 and the second structural member 143.

In some embodiments, the electronic vaporizer further includes a vibration unit. When the first structural member 141 is electrically connected to the second structural member 143 through the solid aerosol-generation substrate 200, the vibration unit vibrates, to remind a user that the aerosol-generation substrate 200 has been inserted into a correct position, thereby preventing the user from continuing to exert a force to cause the aerosol-generation substrate 200 to be deformed and damaged after the aerosol-generation substrate 200 is in contact with the first structural member 141.

The heating assembly 110 and the electronic vaporizer performs insertion detection by using the principle that the aerosol-generation substrate 200 improves the electrical conductivity between the first conductive region and the second conductive region. The heating assembly and the electronic vaporizer have simple structures and relatively high reliability, thus causing no damage to the aerosol-generation substrate 200. In addition, the heating assembly 110 can accurately detects whether the aerosol-generation substrate 200 is inserted into the bottom portion of the heating cavity 147, and provides a feedback to the user through vibration, thereby preventing the heating effect from being affected because the heating position is offset, and preventing the aerosol-generation substrate 200 from being deformed due to an excessive force exerted by the user, and ensuring good inhaling taste.

The technical features in the foregoing embodiments may be randomly combined. For concise description, not all possible combinations of the technical features in the embodiments are described. However, provided that combinations of the technical features do not conflict with each other, the combinations of the technical features are considered as falling within the scope described in this specification.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A heating assembly configured to heat an aerosol-generation substrate, comprising:

a heating cavity configured to accommodate the aerosol-generation substrate, comprising:

a first conductive region;

a second conductive region provided on a side of the first conductive region, the first conductive region and the second conductive region respectively used as a transceiver for performing capacitive sensing and a transceiver for performing resistance measurement, to receive and transmit a capacitive sensing signal and a resistance change signal; and an insulating region provided between the first conductive region and the second conductive region and configured to electrically isolate the first conductive region from the second conductive region, wherein, in a state where the aerosol-generation substrate is accommodated in the heating cavity, an electrical connection is formed between the first conductive region and the second conductive region through the aerosol-generation substrate, and the heating assembly excludes an electromagnetic induction coil.

2. The heating assembly of claim 1, wherein the heating cavity comprises a first end and a second end that are arranged opposite from each other, wherein the aerosol-generation substrate is insertable into the second end of the heating cavity from the first end of the heating cavity, and wherein the aerosol-generation substrate first comes into contact with the first conductive region, and then comes into contact with the second conductive region when it is inserted.

3. The heating assembly of claim 1, wherein the first conductive region is provided at the second end of the heating cavity, and wherein the second conductive region is provided on a cavity side wall of the heating cavity.

4. The heating assembly of claim 3, wherein one end of the second conductive region is connected to the insulating region, and another end of the second conductive region extends to the first end of the heating cavity in a direction away from the insulating region.

5. The heating assembly of claim 1, further comprising:

a first structural member;

a second structural member; and an insulating member, wherein the first structural member forms a part of a cavity bottom wall of the heating cavity, and at least a part of the first structural member forms the first conductive region, wherein the second structural member forms a part of a cavity side wall of the heating cavity, and at least a part of the second structural member forms the second conductive region, and wherein the insulating member is arranged between the first structural member and the second structural member, the insulating member forming the insulating region.

6. The heating assembly of claim 5, wherein the first structural member comprises a conductive material, and/or wherein the second structural member comprises a conductive material.

7. The heating assembly of claim 5, wherein the insulating member comprises an insulating bottom wall and an insulating side wall formed by extending from the insulating bottom wall in a same direction, wherein the insulating side wall surrounds the insulating bottom wall in a circumferential direction to form an insulating accommodating cavity, wherein the insulating bottom wall is provided with a run-through mounting hole in communication with the insulating accommodating cavity, and wherein the first structural member is accommodated in the mounting hole.

8. The heating assembly of claim 7, wherein an inner diameter of the mounting hole is less than an inner diameter of the insulating accommodating cavity.

9. An electronic vaporizer, comprising:

a battery assembly; and the heating assembly of claim 1, wherein the heating assembly is electrically connected to the battery assembly.

10. The electronic vaporizer of claim 9, further comprising:

a vibration unit, wherein, when the first structural member and the second structural member transmit electrical signals through the aerosol-generation substrate, the vibration unit vibrates.

11. The electronic vaporizer of claim 10, further comprising a detection unit electrically connected to the heating assembly and configured to detect a capacitive sensing signal and a resistance signal between the first conductive region and the second conductive region, and to output an insertion signal according to the capacitive sensing signal and the resistance signal.

12. The electronic vaporizer of claim 11, wherein the vaporizer excludes a control button for outputting insertion signals for the aerosol-generation substrate.

13. The electronic vaporizer of claim 11, wherein the vaporizer excludes a squeeze-type mechanical switches for generating the insertion signals when the aerosol-generation substrates are inserted into the electronic vaporizers.

14. The electronic vaporizer of claim 11, wherein the vaporizer excludes a photoelectric switch for generating insertion signals after the aerosol-generation substrates are inserted into the electronic vaporizers.

15. The electronic vaporizer of claim 9, further comprising a detection unit electrically connected to the heating assembly and configured to detect a capacitive sensing signal and a resistance signal between the first conductive region and the second conductive region, and to output an insertion signal according to the capacitive sensing signal and the resistance signal.

16. The electronic vaporizer of claim 15, wherein the vaporizer excludes a control button for outputting insertion signals for the aerosol-generation substrate.

17. The electronic vaporizer of claim 15, wherein the vaporizer excludes a squeeze-type mechanical switches for generating the insertion signals when the aerosol-generation substrates are inserted into the electronic vaporizers.

18. The electronic vaporizer of claim 15, wherein the vaporizer excludes a photoelectric switch for generating insertion signals after the aerosol-generation substrates are inserted into the electronic vaporizers.

* * * * *